US006204044B1

(12) United States Patent
Brown

(10) Patent No.: US 6,204,044 B1
(45) Date of Patent: *Mar. 20, 2001

(54) HUMAN PARVOVIRUS B19 PROTEINS AND VIRUS-LIKE PARTICLES, THEIR PRODUCTION AND THEIR USE IN DIAGNOSTIC ASSAYS AND VACCINES

(76) Inventor: Caroline Sarah Brown, Frans van Mierisstraat 85 huis, Amsterdam (NL), 1071 RM (*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/465,747

(22) Filed: Jun. 6, 1995

Related U.S. Application Data

(63) Continuation of application No. 08/242,023, filed on May 11, 1994, now abandoned, which is a continuation of application No. 07/838,715, filed on May 4, 1992, now abandoned.

(30) Foreign Application Priority Data

Sep. 14, 1989 (NL) .................................................. 8902301
Sep. 11, 1990 (WO) .................................. PCT/NL90/00130

(51) Int. Cl.[7] ............................ C12N 7/00; A61K 39/23; C12Q 1/70

(52) U.S. Cl. .................................... 435/235.1; 424/233.1; 435/5

(58) Field of Search ............................. 424/233.1, 204.1; 435/235.1, 5; 935/65

(56) References Cited

U.S. PATENT DOCUMENTS 4,971,793 * 11/1990 Wood et al. ....................... 424/233.1
5,508,186 4/1996 Young et al. ..................... 435/235.1

FOREIGN PATENT DOCUMENTS

8802026 * 3/1988 (WO) .
90/05538 5/1990 (WO) .

OTHER PUBLICATIONS

French, T.J. et al. Journal of Virology, vol. 64, p. 1530–1536, Apr. 1990.*

Ozawa, K. et al. Journal of Biological Chemistry, vol. 263, p. 10922–10926, 1988.*

Carter, B. et al. "Parvoviridae". In: Animal Virus Structure, ed. Nermut/Stevens, Elsevier Science Publications, 1987.*

Bansal et al. Vaccines 92, p. 315–319. Cold Spring Harbor Laboratory, Cold Spring Harbor NY, 1992.*

Kajigaya et al 1989. A Genetically Engineered Cell Line That Produces Empty Capsids of B19 (Human) Parvovirus. Proc. Natl. Acad. Sci. 86:7601–7605.*

Ozawa et al 1987. Characterization of Capsid & Noncapsid Proteins of B19 Parvovirus Propagated in Human Erythroid Bone Marrow Cell Cultures J. Virol. 61(8):2627–2630.*

Ozawa et al 1987. Novel Transcription Map for the B19 (Human) Pathogenic Parvovirus. J. Virol. 61(8):2395–2406.*

Sisk et al. 1987. Expression of Human Parvovirus B19 Structural Protein in *E. Coli.* & Detection of Antiviral Antibodies in Human Serum. Bio/Technology vol. 5 p. 1077–1080.*

(List continued on next page.)

*Primary Examiner*—Mary E. Mosher

(57) ABSTRACT

The invention relates to the coat proteins VP1 and VP2 of the human parvovirus B19 and virus-like particles consisting of VP2 or of VP1 and VP2. The invention further comprises genetic information in the form of recombinant expression vectors which contain the genes coding for said proteins, and organisms which through genetic manipulation using such vectors have acquired the ability to produce such proteins and/or particles. The invention further comprises uses of such proteins and virus-like particles for diagnostics or vaccination.

1 Claim, 1 Drawing Sheet

OTHER PUBLICATIONS

Cotmore et al. 1986. Identification of the Major Structural & Nonstructural Proteins Encoded by Human Parvovirus B19 & Mapping of Their Genes by Procaryonic Expression of Isolated Genomic Fragments. J. Virol. 60(2):548–557.*

Smith et al 1983. Production of Human B–Interferon in Insect Cells Infected With a Baculovirus Expression Vector. Mol. & Cellular Biolog. 3(12):2156–2165.*

Pennock et al. 1984. Strong & Regulated Expression of *Escherichia Coli* β–Galactosidase in Insect Cells w/a Bacolovirus Vector. Mol. & Cellular Biolog. 4(3):399–406.*

Luckow et al. 1988. Trends in the Development of Baculovirus Expression Vectors. Bio/Technology 6:47–55.*

Pintel et al. 1984. Expression of Minute Virus of Mice Structural Proteins in Morine Cell Lines Transformed by Bovine Pappillomavirus Minute Virus of Mice Plasmid Chimera. J. Virol. 52(2):320–327.*

Evans et al. 1989. An Engineered Poliovirus Chimaera Eliclis Brocdley Reactive HIV–1 Neutralizing Antibodies. Nature 339:385–388.*

Borisova et al. 1989. Recombinant Core Particles of Hepatitis B Virus Exposing Foreign Antigenic Determinants on Their Surface. PEBS Letters. 259(1):121–124.*

Clarke et al. 1987. Improved Immunogenicity of a Peptide Epitope After Fusion to Hepatitis B. Core Protein. Nature 330:381–384.*

Ellis, R.W. et al. 1988. In: Vaccines, Plotkin & Mortimer Eds. W.B. Saundus Co. p. 568–575.*

Collett et al, Rev. Med. Vir. 4: 91–103 (1994).

Brown et al, Vir. Res., 15: 197–212 (1990).

Chapman et al, Virology, 194: 491–508 (1993).

Agbandje et al, Virology, 203: 106–115 (1994).

Cotmore et al, Science, 26: 1161–1165 (1984).

Cossart et al, The Lancet, Jan. 11, 1975, pp. 72–73.

* cited by examiner

HUMAN PARVOVIRUS B19 PROTEINS AND VIRUS-LIKE PARTICLES, THEIR PRODUCTION AND THEIR USE IN DIAGNOSTIC ASSAYS AND VACCINES

This is a continuation of my application Ser. No. 08/242,023, filed May 11, 1994, now abandoned, which is a continuation of my application Ser. No. 07/838,715, filed May 4, 1992, which is a U.S. national stage application under 35 USC 371 of international application PCT/NL90/00130, filed Sep. 11, 1990.

The invention relates both to the field of genetic manipulation by means of the recombinant DNA technology for the production of certain proteins and/or particles that consist of one or more of these proteins, and to the fields of diagnostics and vaccine preparation. The invention concerns certain viral proteins, which may or may not be in the form of virus-like particles, which proteins or particles can for instance be used in assays for detecting antibodies directed against these proteins, or can be used to obtain such antibodies, or can be used to accomplish protection against the virus, or can be used for the incorporation therein of epitopes of proteins of other pathogenes to accomplish protection against these other pathogenes (and thus offers various possibilities of use for vaccination purposes).

More particularly, the invention relates to the coat proteins VP1 and VP2 of the human parvovirus B19 and to virus-like particles that consist of VP2 or of VP1 and VP2. The invention further comprises genetic information in the form of recombinant expression vectors which contain the genes coding for these proteins, and organisms that have acquired the ability to produce the proteins and/or particles in question owing to genetic manipulation using such vectors.

The human parvovirus B19 was serendipitously discovered in 1975 in serum samples of some healthy blood donors. Since that time it has been found that the virus causes erythema infectiosium—also known as "fifth disease"—and of the so-called "aplastic crisis" in patients with chronic hemolytic anemia. The B19 virus is further associated with abortion and fetal death, with arthritis and with chronic anemia in immuno-deficient patients. Infections may also occur under other syndromes or occur entirely asymptomatically.

Infections with this virus, which is found throughout the world, usually occur in epidemics which take place about every 3–6 years, but may occur sporadically in intervening years. Today, fourteen years after the discovery of the B19 virus, the diagnostics for infection with the virus are still performed in only a limited number of laboratories in the world. Because the virus cannot be demonstrated anymore in the patients at the time when the symptoms arise (viremia and virus excretion precede the symptoms), diagnostics must focus on demonstrating B19-specific (IgM)-antibodies.

To this end (and also for the preparation of suitable vaccines, for example) it is necessary to have a sufficient supply of B19-antigen for setting up the tests. What is lacking, however, is a suitable in vitro cell culture system for propagating the virus, with which sufficient antigen can be obtained.

The existing parvovirus B19 diagnostics are performed with virus antigen which becomes available more or less by chance (screening blood donors offers an estimated chance of 1 in 50,000 that viremic blood is found).

For these reasons there is a great need for antigen which is produced using recombinant DNA techniques. Accordingly, various proposals in this direction have already been made, but none of them has proved really useful for the construction of a diagnostic test.

The present invention is based on the use of an expression vector system that was developed fairly recently, viz. the "Baculovirus Expression Vector System". In this system use is made of a recombinant virus vector of the baculo-virus *Autographica californica* nuclear polyhedrosis virus (AcNPV) to express the B19 virus proteins in insect cells: *Spodoptera frugiverda* (Sf9). This system offers many advantages over the current systems of expression vectors:

a) In view of the use for diagnostic and possibly therapeutic (vaccination) purposes, no cross reactivity is to be expected against proteins of the baculovirus or the insect cells (in proteins which are expressed in *E. coli*, this cannot always be precluded).

b) The virus proteins can be produced in large amounts (1–500 mg/l) up to even 50–75% of the total protein, detected on SDS-polyacrylamide gel (Summers and Smith, 1986, a manual of methods for baculovirus vector and insect cell culture procedures; Yong Kang, 1988; Adv. in Virus Res. 35, 177–192). These are considerably larger amounts than those produced in prokaryotic expression systems or in Chinese hamster ovary cells, as described by Kajigaya et al. (Blood 75(5), suppl. 1, 44a, abstr. 86; 1988).

c) The proteins can be produced as non-fusion proteins, in contrast to for instance the B19 protein, which has been produced as a fusion protein in *E. coli* by Sisk and Berman (Biotechnology 5, 1077–1080, 1987). This recombinant β-galactosidase-B19 fusion protein goes into solution only in the presence of sodium dodecylsulphate (SDS). The proteins VP1 and VP2 expressed in insect cells in accordance with the invention, by contrast, can easily be dissolved by sonification of the cells in a buffer which contains 25 mM $NaHCO_3$ and 20 mg/l $NaN_3$ (pH 9.5). In such a treatment 95% of the cellular proteins go over into the soluble supernatant fraction.

d) The proteins can be produced in an insect cell line which is easy to culture, as opposed to the production of virus proteins in human erythroid bone marrow cells (Ozawa et al., 1987; Blood 70, 384–391) or human foetal erythroid liver cells (Yaegashi et al., 1989; J. Virol. 63, 2422–2426).

e) Because in the baculovirus expression vector system pre- and post-translation modifications occur, such as phosphorylation, glycosylation, signal peptide split-off and the removal of introns by splicing, the system is potentially very suitable for the production of biologically active proteins with a (virtually) native structure (Yong Kang, 1988; Adv. in Virus Res. 35, 177–192). In this system VP1 and VP2 of B19 can be expressed both separately and collectively. Moreover, the possibility exists that virus-like particles are spontaneously formed from one or more of these proteins.

f) An additional advantage of the baculovirus is that it does not multiply in mammalian cells and hence is not pathogenic for humans, which makes it much safer to work with and utilize this system.

According to the invention it has actually been accomplished to produce in a high yield the coat proteins VP1 and VP2 of the human parvovirus B19 in an antigenically active form as non-fusion proteins, as virus-like particles or not, using the baculovirus expression system in insect cells (*Spodontera frugierda*). Further, it has been accomplished to develop, using the B19 virus proteins producing insect cells, a specific and sensitive immunofluorescence-assay (IFA) and a specific and sensitive Enzyme-Linked-Immuno-Sorbent-Assay (ELISA) for the detection of antibodies directed against the B19 virus proteins. However, on the basis of the B19 virus proteins and virus-like particles produced in insect cells in conformity with the invention, other diagnostic assays can be developed as well, such as a Radio-Immuno-Assay (RIA) or an agglutination test.

The invention is primarily embodied in recombinant VP1 and VP2 protein of the human parvovirus B19, formed in *Spodoptera frugiperda* cells which, by means of a baculovirus expression vector system, have been equipped with the genetic information necessary for expression of the B19 virus protein VP1 and/or VP2. The invention further comprises recombinant virus-like particles which consist of VP2 protein or of VP1 and VP2 protein of the human parvovirus B19, formed in *Spodontera frugiperda* cells which, by means of a baculovirus expression vector system, have been equipped with the genetic information necessary for expression of VP2 protein or of VP1 and VP2 protein.

Further, the invention is embodied in *Spodoptera frugiperda* cells which, by means of a baculovirus expression vector system, have been equipped with the genetic information which is necessary for expression of VP1 and/or VP2 protein of the human parvovirus B19.

The invention further provides a method of producing VP1 and/or VP2 protein of the human parvovirus B19 (optionally in the form of virus-like particles which are composed of VP2 protein or of both proteins) by culturing *Spodoptera frugirerda* cells which, by means of a baculovirus expression vector system, have been equipped with the genetic information which is necessary for expression of the B19 virus protein or the B19 virus proteins. Optionally and preferably the B19 virus protein formed in the cells and/or the virus-like particles formed in the cells and consisting of VP2 protein or of VP1 and VP2 protein are isolated from the cells. A suitable method for that purpose comprises a sonification of the cells in a buffer which contains 25 mM $NaHCO_3$ and 20 mg/l $NaN_3$ (pH 9.5). The result of such a treatment is that a great part of the proteins present in the cells, for instance 95%, are obtained in dissolved form in the supernatant. By known per se purification methods, the B19 virus proteins can be isolated at a higher purity.

The invention is also embodied in recombinant baculovirus expression vectors, equipped with the genetic information which is necessary for expression of VP1 and/or VP2 protein of the human parvovirus B19 in *Spodoptera frugiperda* cells. Preferred embodiments of such recombinant baculovirus expression vectors are the plasmids pAcB19VP1-YM1 and pAcB19VP2-YM1, to be described hereinafter.

The invention is further embodied in recombinant baculoviruses, equipped with the genetic information which is necessary for expression of VP1 and/or VP2 protein of the human parvovirus B19 in *Spodoptera frugiperda* cells. Preferred embodiments of such recombinant baculoviruses are the viruses AcB19VP1L and AcB19VP2L, to be described hereinafter.

The invention further comprises the use of recombinant VP1 and/or VP2 protein of the human parvovirus B19, formed in *Spodoptera frugiperda* cells which, by means of a baculovirus expression vector system, have been equipped with the genetic information necessary for expression of the B19 virus protein, in an assay for detecting antibodies directed against the B19 virus protein in a sample to be tested. The invention comprises the use of recombinant virus-like particles which consist of VP2 protein or of VP1 An VP2 protein of the human parvovirus B19, formed in *Spodoptera frugiperda* cells which, by means of a baculovirus expression vector system, have been equipped with the genetic information necessary for expression of these B19 virus proteins, in an assay for detecting antibodies directed against the B19 virus in a sample to be tested. In preferred embodiments of the invention, this concerns the use of *Spodoptera frugiperda* cells which, by means of a baculovirus expression vector system, have been equipped with the genetic information which is necessary for expression of VP1 and/or VP2 protein of the human parvovirus B19, in an assay for detecting antibodies directed against the B19 virus protein in a sample to be tested, more particularly in an IFA or ELISA for detecting antibodies directed against the B19 virus protein in a sample to be tested.

The invention also comprises a vaccine preparation for inducing an immune response which provides protection against the human parvovirus B19, comprising recombinant VP1 and/or VP2 protein of the human parvovirus B19, formed in *Spodoptera frugiperda* cells which, by means of a baculovirus expression vector system, have been equipped with the genetic information necessary for expression of the B19 virus protein, or an antigenically active portion of this recombinant B19 virus protein, in combination with one or more carriers and/or adjuvants suitable for vaccination purposes, and further, a vaccine preparation for inducing an immune response which provides protection against the human parvovirus B19, comprising recombinant virus-like particles which consist of VP2 protein or of VP1 and VP2 protein of the human parvovirus B19, formed in *Spodotera frugiperda* cells which, by means of a baculovirus expression vector system, have been equipped with the genetic information necessary for expression of these B19 virus proteins, in combination with one or more carriers and/or adjuvants suitable for vaccination purposes.

The invention further comprises the use of recombinant VP1 and/or VP2 protein of the human parvovirus B19 (or virus-like particles consisting of VP2 or of VP1 and VP2), formed in *Spodoptera frugiperda* cells which, by means of a baculovirus expression vector system, have been equipped with the genetic information necessary for expression of the B19 virus protein, or with an antigenically active portion of this recombinant B19 virus protein, for inducing an immune response which provides protection against the human parvovirus B19.

The invention also comprises the use of virus-like particles consisting of VP2 protein or VP1 and VP2 protein of the human parvovirus B19, into which one or more epitopes of proteins of other pathogens have been incorporated, for inducing an immune response which provides protection against these other pathogens.

In the experimental section to follow hereinbelow, it is shown by way of explanation and illustration how the invention was carried out and can be carried out. As shown by the Examples, the DNA sequences coding for the structural proteins VP1 and VP2 of the human parvovirus B19 were isolated from the B19 virus from the serum of a patient. Then, via subcloning steps in pUC19 and pUC7, the B19-DNA was cloned into the baculovirus vector pAcYM1 behind the promoter for the polyhedrin gene of the baculovirus. By means of cotransfection of this recombinant vector with wild type baculovirus DNA, followed by recombination in the insect cells (*Spodoptera frugiperda*), finally, recombinant virus was isolated which, after infection in the insect cells, led to the production of the coat proteins VP1 and VP2 of B19, which were or were not in the form of virus-like particles. Using these B19 proteins, sensitive and specific IFA and ELISA tests were developed, enabling fast and simple detection of B19-specific antibodies. The proteins produced in this manner, which may or may not be in the form of virus-like particles, may also serve as easily obtainable antigens for other diagnostic tests, such as RIA's and agglutination tests and for the (possible) production of vaccines and subunit vaccines.

DESCRIPTION OF THE FIGURES

FIG. 1 further shows the cloning diagram for the construction of recombinant baculovirus with human parvorvirus B19 genes.

EXAMPLE 1

Figure 1:
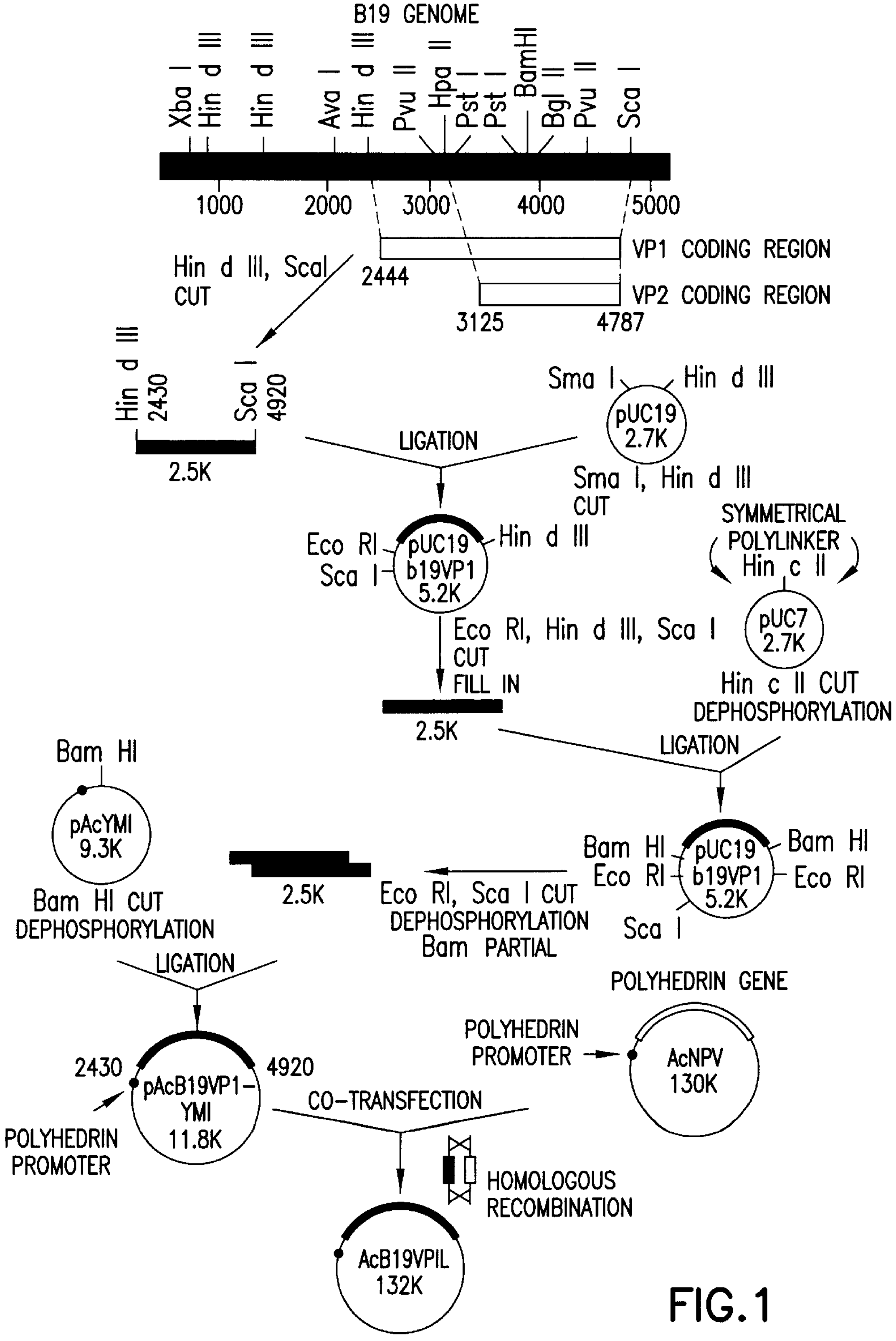
FIG. 1 shows the genetic structure of the human parvovirus B19, which is a single-stranded DNA virus having a DNA of about 5500 nucleotides. According to Ozawa et al., 1987; J. Virol. 61, 2395–2406 the nucleotides 2444–4787 contain the sequence coding for VP1 (84 kd) and the nucleotides 3125–4787 contain the sequence coding for VP2 (58 kd). Not shown are the 4 splicing donor-sites, located between the nucleotides 2177 and 2195, and the 2 acceptor-sites, located between the nucleotides 3043 and 3050. For the production of VP2 during the virus replication, the intermediate sequence (nucleotides 2177–3050, which includes the initiation codon for VP1) is removed by splicing.

Expression of parvovirus B19 VP1.

1. Isolation of parvovirus B19 DNA from patient serum.

After B19 DNA was demonstrated in the serum of a patient by means of the "polymerase chain reaction" and Dot-Spot-Hybridization with B19 specific DNA probes (Salimans et al., 1989; J. Virol. Meth. 23, 19–28) the B19 DNA was isolated from it by incubation with proteinase K and SDS (1 ml serum was incubated at 37° C. for 2 h with 100 $\mu$g proteinase K in a buffer which contained 10 mM Tris-Cl (pH 7.5), 5 mM EDTA and 0.5% SDS), phenol extraction for removing the protein and DNA precipitation by means of ethanol. The DNA was assayed as to size, restriction enzyme patterns and Southern blot analysis (Maniatis et al., 1982; Molecular cloning: a laboratory anual. Cold Spring Harbor, N.Y.) with B19-specific DNA probes.

2. Subcloning into pUC19 (FIG. 1).

The techniques for the manipulations with B19-DNA and plasmid-DNA were essentially carried out as described by Maniatis et al. (1982; Molecular cloning: a laboratory manual). The B19 DNA was cut with HidIII (bp 2430) and ScaI (bp 4920) and ligated into pUC19 (cut with HindIII and SmaI) so as to obtain a larger amount of the coding sequence. (By ligating ScaI in SmaI, this cutting site was removed). The plasmid obtained (pUC19-B19VP1) was assayed by restriction enzyme analysis and hybridization and transformed to and propagated in *E. coli* JM101.

3. Subcloning into pUC7 (FIG. 1).

To create BamHI-sites at the ends of the B19 DNA, the DNA was cloned into pUC7, which contains a symmetrical polylinker with two BamHI-sites. The B19 DNA was cut from pUC19 with HindIII and EcoRI and also with ScaI to remove the residue of the vector DNA. The B19 DNA fragment with the proper length-was isolated from agarose gel, filled in with "Klenow large fragment polymerase" and ligated with HincII cut pUC7 plasmid (also blunt-ended). The ligated DNA (PUC7-B19VP1) was transformed to and propagated in *E. coli* JM101. Separate colonies were tested for the presence of B19 DNA by means of restriction enzyme analysis and hybridization with a B19 specific DNA probe (the 700bp PstI-fragment of B19, Salimans et al., 1989; J. Virol. Meth. 23, 19–28).

4. Cloning into the baculovirus vector pAcYM1 (FIG. 1).

The techniques for manipulations with the baculovirus, the baculovirus vector and the insect cells were essentially performed as described by Summers and Smith in 1986 (a manual of methods for baculovirus vector and insect cell culture procedures). The restriction site following the polyhedrin promoter of the baculovirus is a BamHI-site. Since the B19 DNA also contains an internal BamHI-site, the following strategy was opted for: the B19 DNA was cut from pUC7 with EcoRI and the remaining part of pUC7 was cut with ScaI (this ScaI digestion is not necessary for cloning of VP2 DNA). The B19 DNA was isolated from the gel, dephosphorylized with Calf Intestinal Alkaline Phosphatase (CIP) and finally a partial digestion was performed with BamHI. The BamHI-fragment with the proper length (2.5 kb for VP1 and 1.8 kb for VP2) was then ligated with baculovirus vector pAcYM1, cut with BamHI and treated with CIP (Matsuura et al., 1987; J. Gen. Virol. 68, 1233–1250). The plasmid (pAcB19VP1-YM1) thus obtained was propagated in *E coli* HB101. Recombinant plasmids were analyzed for the presence of B19 DNA (with specific B19 DNA probes) and the proper orientation thereof relative to the polyhedrin promoter (by means of restriction enzyme analysis). Constructs with the proper orientation were cultured and isolated from the bacterial cells according to "the rapid boiling" method of Holmes and Quigley (1981; Anal. Bioch. 114, 193–197) with a final purification on a CsCl-gradient.

5. Cotransfection with wild type baculovirus DNA: AcNPV (FIG. 1).

By means of a cotransfection of the pAcB19VP1-YM1 construct with wild type baculovirus DNA (AcNPV) the DNA was introduced into the insect cells (*Spodoptera frugiperda*-Sf) (according to method II of Summers and Smith, 1986; a manual of methods for baculovirus vector and insect cell culture procedures). In 0.5–3.0% of the infections, the recombinant vector (pAcB19VP1-YM1) recombines with the wild type virus DNA during the uptake into the cells, thus generating a recombinant virus which contains the B19 DNA: AcB19VP1L. The polyhedrin gene has been replaced by the VP1 DNA (in Example 2, in which the formation of a recombinant virus AcB19VP2L is described, by the VP2 DNA).

6. Purification of recombinant virus (AcB19VP1L and AcB19VP2L).

The titre of the virus (both wild type and recombinant) produced by the Sf cells was determined by means of a plaque assay. Twenty plaque-forming units (pfu) were placed on a monolayer of Sf-cells in a 96-well plate (20 pfu/well) and incubated at 27° C. Three days after the infection the supernatants were removed and retained and the cells were lysed and spotted on nitrocellulose (Pet et al., 1989; Nucl. Acid Res. 17, 451). Screening for the presence of recombinant virus was performed with a parvovirus B19-specific DNA probe. The titre of the wells containing the collected supernatants of recombinant virus was determined by means of a plaque assay and then diluted to 1 pfu/well on a 96-well plate. After a screening as described hereinabove with the dot-spot-hybridization assay the titre of the positive supernatants was determined in a plaque assay and furthermore screening for the absence of the polyhedrin protein in the plaques was done with a microscope, indicating that the plaque contains recombinant virus. These plaques were inoculated on a Sf-monolayer in a 96-well plate. After three days dot-spot-hybridization was repeated and positive wells were assayed in a plaque assay. The recombinants were considered pure when less than 1 in 500 plaques contained wild type virus.

7. Assay of the recombinant virus (AcB19VP1L).

From cells infected with recombinant virus, total DNA was isolated, cut with restriction enzymes and following Southern blotting assayed by hybridization with parvovirus B19-specific DNA probes.

Pure recombinant virus was used to infect insect cells (Sf) with an m.o.i. (multiplicity of infection) of 1–5 and to express parvovirus VP1 and VP2 in these cells. Then the coat proteins VP1 and VP2 of the human parvovirus B19, produced in the baculovirus expression vector system, were analyzed and assayed with the techniques described hereinbelow:

8. Biosynthesis of recombinant VP1.

Two days after infection with recombinant virus (AcB19VP1L, m.o.i. 5) insect cells ($10^6$ Sf-cells in 35 mm-Petri dish) were cultured for 4 h at 27° C. in methionine-free “Grace”-medium to which 100 uCi $^{35}$S-methionine had been added, for determining the de novo synthesis of proteins. After the supernatant was discarded, the cells were placed in PBS (phosphate buffered saline). Both supernatant and cell fraction were placed in lysing buffer, boiled for 5 min and analyzed on a 10% SDS-polyacrylamide gel. The same experiments were performed with uninfected and wild type baculovirus-infected cells. Autoradiography (not shown) revealed that the polyhedrin band (30kd) which dominated strongly in the wild type infection, disappeared in the recombinant viruses and that a protein of the size of the VP1 of B19 (84 kd) was synthesized.

9. Analysis for SDS-PAGE

After infection with recombinant virus (m.o.i.5) *Spodoptera frugiperda* cells were analyzed for 5 days for the production of VP1 of B19 virus on 10% SDS-polyacrylamide gel. The gels were stained with “fast green”. The gel results (not shown) revealed that from day 2 VP1 was produced in large amounts as a stable product which was still clearly present after 5 days. VP1 was produced in comparable amounts to those of the polyhedrin protein in wild type baculovirus-infected cells.

10. Antigenicity of the produced proteins.

100 ng of protein of cell lysates of Sf-cells 2 days after infection (m.o.i.5) was subjected to electrophoresis on 10% SDS-polyacrylamide gel and blotted to nitrocellulose (3 h; 70 V in 25 mM Tris, 192 mM glycine and 20% methanol). Then 20 human sera were tested for reactivity with the recombinant VP1 antigen (15 IgG-positive sera and 5 IgG negative sera). The reactions were performed at room temperature: overnight blocking by incubation of the nitrocellulose filter in PBS/5% Foetal Calf Serum (FCS)/ 0.05% Tween 20; incubation with sera (1:500 dilution for the positive sera and 1:50 dilution for the negative sera) diluted in PBS/5% FCS for 1.5 h; followed by washing of the filters for 1 h with PBS/0.05% Tween 20 and then incubation with 1:500 diluted alkaline phosphatase labelled goat-anti-human-total Ig (Tago, cat. no.: 2493) in PBS/0.05% Tween 20/ 5% FCS; after washing 2x in PBS/ 0.05% Tween 20 and 2x in PBS, bound antibodies were detected with 5-bromo-4-chloro-3-indolyl phosphate (BCIP). The 15 positive IgG sera all reacted with the recombinant VPl band on the gel and the 5 negative IgG sera did not yield any reaction.

11. Testing sera in an immunofluorescence assay.

Sf-cells infected with recombinant virus (AcB19VP1L, m.o.i.1) were placed in TC100 medium (Gibco-BRL) after 3–4 days, mixed with uninfected cells up to a percentage of approximately 25% of cells containing B19 recombinant VP1 and spotted on 18-well glass plates (nutacon, cat. no. 10-404) with a concentration of approximately 500 cells/ well (5 $\mu$l) and after drying in the air fixated in 100% acetone for 20 min at −20° C. Then the cells were incubated with human sera (positive and negative sera for B19-Ig) at different dilutions in VBS (veronal buffered saline). These sera were pretreated with liver powder for a reduction of possible background colouring. After incubation for 1–2 h at 37° C. the glass plates were washed in PBS and dried in the air before incubation with a 1:40 dilution of FITC-labelled goat-anti-human-IgG (Kallestad, cat. no.: 104) in VBS with 1:500 “Evans Blue” (Hoffmann La Roche). After washing in PBS and drying in the air Tris/glycerol buffer (1 g Tris in PBS, 80% glycerol, pH 9.9) was added and analysis done under the UV-microscope. In B19-IFA’s with positive patient sera the fluorescent cells could be observed. The usefulness of the B19-IFA was tested in a number of experiments as described hereinbelow:

a) “Double-blind” experiment.

30 patient sera were tested according to the procedure in 1:50 and 1:500 dilutions, without the “investigator” knowing which of the sera were positive and which were negative. After reading by several co-workers the results were compared with the data from the RIA test (Cohen et al., 1983; J. Hyg. 91, 113–130): in the B19-IFA all 17 IgG-positive sera were read as positive and all 13 IgG-negative sera as negative.

b) Titration.

Of a number of B19-antibody positive sera (positive according to the test results of the RIA, performed with virus isolated from serum as antigen, Cohen et al., 1983; J. Hyg. 91, 113–130) an IFA-titre was determined. Results are summarized in Table 1. The data reveal that this B19-IFA yields results corresponding to the RIA data: sera with high positive values in the RIA also have high titres in the B19-IFA and sera with low positive values in the RIA yield lower titres in the B19-IFA.

TABLE 1

Comparison between RIA and IFA for the assay of B19 antibodies

| IgG RIA (a.u.) | IFA (titre) | IgM RIA (a.u.) | IFA (titre) |
|---|---|---|---|
| 100 | 8192 | >100 | 1280 |
| 100 | >16384 | 88 | 1280 |
| 91 | >16384 | 50 | 1280 |
| 70 | 8192 | 31 | 2560 |
| 55 | 8192 | 25 | 1280 |
| 40 | 8192 | 16 | 640 |
| 25 | 8192 | 16 | 320 |
| 15.5 | 4096 | 8.3 | 40 |
| 11 | 4096 | 5.3 | <10 |
| 8.4 | 1024 | 5 | 80 |
| 7.6 | 512 | 4.4 | 10 |
| 4.2 | 512 | 4.1 | 40 |
| 4.0 | 512 | 3.1 | 10 |
| 2.5 | <32 | 3.4/2.9 | <10 |
| 1.8 | 128 | 3.3 | 160 |
| 1.2 | <32 | 2.3/1.9 | <10 |
| <1 | <32 | 1.6 | <10 |
| <1 | <32 | <1 | <10 |
| <1 | <32 | <1 | <10 |

a.u. = arbitrary units; <1 = negative value RIA; <32 = negative value IFA at lowest dilution of IgG; <10 = negative value IFA at lowest dilution of IGM.

c) Screening of donors.

100 randomly selected blood donors were screened for the presence of B19-specific IgG antibodies and the results showed that in this B19-IFA 76% of the donors were positive, which corresponds very well with the data as described for the human parvovirus B19 for this age-group.

EXAMPLE 2

Expression of parvovirus B19 VP2.

Subcloning of VP2 into pUC7.

Cloning of the VP2 of parvovirus B19 started from the B19 DNA that has been cloned into pUC19 according to the procedure as described in Example 1 under points 1 and 2. A 1.8 kb fragment, coding for VP2, was cut from the pUC19 construct (pUC19-B19VP1) with HpaII (bp 3083) and EcoRI, isolated from agarose gel, filled in with "Klenow large fragment DNA polymerase" and ligated with pUC7 plasmid cut with HincII. The new pUC7 construct (pUC7-B19VP2) was then propagated in *E. coli* JM101. Bacterium colonies were then tested for the presence of a B19-insertion by means of restriction enzyme analysis and hybridization with a B19-specific DNA probe (Salimans et al., 1989; J. Virol. Meth. 23, 19–28). Further, the same procedure was followed as described for VP1 in Example 1 under points 4–7 to generate recombinant baculovirus with the DNA coding for VP2 of the human parvovirus and to produce VP2 in the insect cells (AcB19VP2L)

EXAMPLE 3

Expression of parvovirus B19 VP1 and VP2 using double infection of insect cells

Two days after infection with the recombinant viruses (AcB19VP1L and AcB19VP2L, m.o.i. 5) insect cells ($10^6$ Sf-cells in 35 mm Petri-dish) were cultured for 4 h at 27° C. in methionine-free "Grace" medium to which 100 $\mu$Ci $^{35}$S-methionine had been added, to determine the de novo synthesis of proteins. After the supernatant was discarded, the cells were placed in PBS (phosphate buffered saline). Both supernatant and cell fraction were placed in lysing buffer, boiled for 5 min and analyzed on a 10% SDS-polyacrylamide gel. The same experiments were performed with uninfected and wild type baculovirus-infected cells. Autoradiography (not shown) revealed that the polyhedrin band (30 kd), which dominated strongly in the wild type infection, disappeared in the cells infected with the recombinant viruses and that proteins of a size of the VP1 (84 kD) and the VP2 (58 kD) of B19 were synthesized. The results were confirmed by SDS-PAGE analysis as described in Example 1 under point 9.

EXAMPLE 4

Production and purification of VP2 capsid protein of human parvo virus strain B19

Sf-cells were infected with the VP2-recombinant baculovirus (m.o.i. 20). 72 h after the initiation of the infection the cells were washed in PBS, harvested and then sonicated in PBS. Cell debris was removed by means of centrifugation (10 min, 1,000 x g), after which the supernatant was placed on a 40% sucrose cushion and centrifugation was performed for 2.5 h at 100,000 x g. The pellet was resuspended in PBS and then separated on a linear sucrose gradient (15–30%, w/w). After centrifugation for 2.5 h at 110,000 x g an opalescent band was observed. Material from this band was examined by electron microscopy. Particles were found that showed great similarity to the parvovirus capsid as to diameter (approximately 21 nm) and morphology. After analysis of the sucrose gradient fraction by means of SDS-PAGE and silver staining a protein was found of the size of VP2 (58 K). By means of radio-immuno-precipitation and Western blot analysis with a human serum, specific for parvovirus B19, it was demonstrated that the VP2 protein is indeed involved here. The fact that after silver staining no other proteins were detected points to a high degree of purity. The amount of protein in the gradient fractions enriched for the particles was determined by means of the Bradford procedure. On the basis of the data obtained the number of particles per infected insect cell was estimated at at least $10^5$, it being assumed that each particle is made up of 60 molecules. To determine whether the purified VP2 particles can be used for setting up a diagnostic test, an ELISA was performed with 8 B19-positive and 3 B19-negative human sera. In Table 2 the results are compared with those obtained for purified recombinant VP1 protein. All B19-positive sera recognized the VP2 capsids. Moreover, for seven of the eight sera the reaction with the VP2 capsids proved more strongly positive than that with the purified VP1 protein.

TABLE 2

ELISA for demonstrating parvovirus-specific antibodies in 11 human sera with recombinant VP1 and VP2 protein as antigens

| Extinction* | number of sera purified VP1 | VP2 particles |
|---|---|---|
| <0.5 | 3 | 3 |
| 0.5–1.0 | 2 | 0 |
| 1.0–2.0 | 5 | 0 |
| >2.0 | 1 | 8 |

*Extinction <0.5: negative; >0.5: positive

What is claimed is:

1. Isolated and purified VP1 capsid protein of the human parvovirus B19, which has been expressed in and isolated from *Spodoptera frugiperda* cells which by means of a barculovirus, expression vector system have been provided with the genetic information which is necessary for expression of said capsid protein.

* * * * *